(12) United States Patent
McCoy et al.

(10) Patent No.: US 9,271,928 B2
(45) Date of Patent: Mar. 1, 2016

(54) DRUG DELIVERY COMPOSITION

(75) Inventors: Colin Peter McCoy, South Belfast (GB); Sean Patrick Gorman, Downpatrick (GB); David Simon Jones, Newtonabbey (GB)

(73) Assignee: THE QUEEN'S UNIVERSITY OF BELFAST, Belfast (GB)

( * ) Notice: Subject to any disclaimer, the term of this patent is extended or adjusted under 35 U.S.C. 154(b) by 336 days.

(21) Appl. No.: 12/996,041

(22) PCT Filed: May 28, 2009

(86) PCT No.: PCT/GB2009/001338
§ 371 (c)(1),
(2), (4) Date: Jan. 12, 2011

(87) PCT Pub. No.: WO2009/147372
PCT Pub. Date: Dec. 10, 2009

(65) Prior Publication Data
US 2011/0165114 A1    Jul. 7, 2011

(30) Foreign Application Priority Data
Jun. 6, 2008   (GB) .................................. 0810359.0

(51) Int. Cl.
*A61K 9/00* (2006.01)
*A61K 41/00* (2006.01)
*A61L 27/34* (2006.01)
*A61L 27/54* (2006.01)
(Continued)

(52) U.S. Cl.
CPC ............ *A61K 9/0024* (2013.01); *A61K 41/0042* (2013.01); *A61L 27/34* (2013.01); *A61L 27/54* (2013.01); *A61L 29/085* (2013.01); *A61L 29/16* (2013.01); *A61L 2300/406* (2013.01); *A61L 2300/602* (2013.01)

(58) Field of Classification Search
CPC ....... A61L 27/34; A61L 27/54; A61L 29/085; A61L 29/16; A61L 2300/406; A61L 2300/602; A61K 9/0024; A61K 41/0042
See application file for complete search history.

(56) References Cited

U.S. PATENT DOCUMENTS 5,470,307 A   11/1995   Lindall

FOREIGN PATENT DOCUMENTS

| AU | 785289 B2 | 12/2006 | |
| WO | WO 94/09826 | * 5/1994 | ............ A61K 41/00 |
| WO | WO-94/09826 A2 | 5/1994 | |

(Continued)

OTHER PUBLICATIONS

Kim, Häertner Hammp, "Two-photon triggered drug delivery system: A new way to prevent posterior capsule opacification", Proc. of spie, vol. 6138, 2006 XP040219987 DOI: 10.1117/12.646098, 8 pages.

(Continued)

*Primary Examiner* — Trevor Love
(74) *Attorney, Agent, or Firm* — Winstead PC

(57) ABSTRACT

There is provided a non-water soluble drug delivery composition comprising a conjugate and a polymer matrix wherein exposure of the composition to electromagnetic radiation at a suitable pre-determined wavelength and intensity induces release of the active ingredient from the composition. The conjugate is attached to the polymer matrix through non-covalent interactions. There is also provided a drug delivery apparatus formed from the drug delivery composition.

31 Claims, 1 Drawing Sheet

Figure 1:
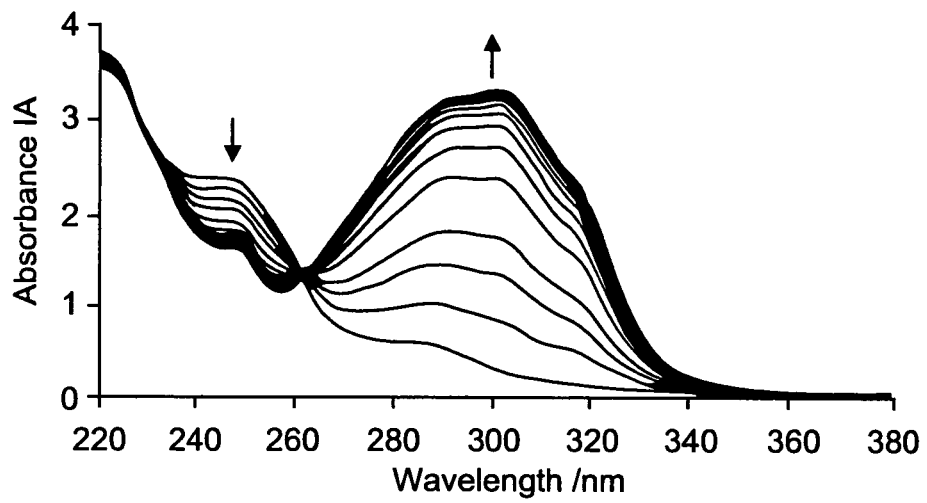

(51) Int. Cl.
*A61L 29/08* (2006.01)
*A61L 29/16* (2006.01)

(56) References Cited

FOREIGN PATENT DOCUMENTS

| WO | WO-96/23543 A1 | 8/1996 |
| WO | WO-2006/019848 A1 | 2/2006 |
| WO | WO-2006/089007 A2 | 8/2006 |
| WO | WO-2006/128121 A2 | 11/2006 |
| WO | WO-2007/085804 A1 | 8/2007 |

OTHER PUBLICATIONS

Van De Wetering, P., "International Search Report" for PCT/GB2009/001338 as mailed Sep. 1, 2010, 7 pages.

McCoy, Colin P., et al., "Light-Triggered Molecule-Scale Drug Dosing Devices", J. Am. Chem. Soc., JACS Communications, Published on Web Jul. 18, 2007, 2 pages.

McCoy, Colin P., et al., "Supporting Information for Light-Triggered Molecule-Scale Drug Dosing Devices", J. Am. Chem. Soc., JACS Communications, Published on Web Jul. 18, 2007, 5 pages.

* cited by examiner

DRUG DELIVERY COMPOSITION

The present invention relates to a non-water soluble, polymeric drug delivery composition comprising an active ingredient, said active ingredient being controllably and predictably releasable upon exposure of the polymeric composition to electromagnetic radiation at a suitable predetermined wavelength and intensity. The present invention also provides the use of such a composition in the manufacture of a drug delivery device, and a drug delivery device comprising such a composition. The present invention further relates to a method of incorporating an active ingredient into a drug delivery device such that, upon exposure of the device to electromagnetic radiation at a suitable predetermined wavelength and intensity, the active ingredient is controllably and predictably released.

The ability to control drug dosing in terms of quantity, location, and time is a key goal for drug delivery science, as improved control maximizes therapeutic effect while minimizing side effects. Systems responsive to a stimulus such as temperature, pH, applied magnetic or electrical field, ultrasound, light, or enzymatic action have been proposed as triggered delivery systems. However, these systems are indirectly triggered, as they induce a macroscopic change in the matrix into which the drug is incorporated. To date, no method to externally, directly trigger precise drug doses to a targeted area has been demonstrated.

A study commissioned by the Department of Health, estimated that hospital acquired (nosocomial) infection may cost the National Health Service almost £1 billion a year and on this basis the National Audit Office estimated possible gross savings of £150 million a year if preventative measures are established. It is accepted that of all nosocomial infection in the intensive care unit (ICU), pneumonia is the most commonly reported in mechanically ventilated patients. Ventilator-associated pneumonia (VAP) refers to a subset of nosocomial pneumonia that arises in patients in whom the pneumonia was neither present nor incubating at intubation and who have been receiving mechanical ventilation via an endotracheal (ET) tube for at least 48 hours. The incidence of VAP can be as high as 67% and the reported mortality of patients with VAP ranges from 24% to 71% despite the use of complex antibiotic regimens. Research has shown the ET tube to be implicated in the pathogenesis of VAP due to the rapid formation of an antibiotic-resistant microbial biofilm on the poly(vinyl chloride) tube. The causal link between medical device biofilm and pneumonia has been demonstrated.

The problem of medical device-related infection is common to all implanted medical devices. Bacteria can colonise medical device polymers and develop extreme antibiotic resistance rapidly by exuding an enveloping, protective exopolysaccharide matrix and entering into a very reduced metabolic mode of existence. The early and abundant microorganism colonisation of implanted medical devices, such as ET tubes has been observed. In particular, the presence of antibiotic-resistant microbial biofilm has been observed. Dissemination of bacterial cells from this biofilm 'reservoir of infective cells' into the body causes infection. In particular, dissemination of bacterial cells into the lower respiratory tract can occur by the passage of the ventilated air, causing the onset of infection.

3,5-Dimethoxybenzoin (3,5-DMB) derivatives have been used previously as protecting groups in organic synthesis. It is known that these groups can be subsequently removed by application of light. Although this photochemical reaction has found applications in synthesis, applications of this method in drug liberation have not been investigated. Furthermore, water insoluble, polymeric matrices comprising 3,5-DMB derivatives are not known.

WO 2006/089007 discloses water-soluble, cyclodextrin-containing biocompatible polymers, covalently attached to bioactive moieties through attachments cleaved under biological or photolytic conditions to release the bioactive moieties. The compositions of WO 2006/089007 allow controlled delivery of the bioactive moieties. Delivery of the bioactive moieties may be targeted into specific cells or tissues. In particular, the compositions of WO 2006/089007 may target tumours, and only release the bioactive moieties attached thereto upon application of radiation to the tumour. All of the compositions disclosed in WO 2006/089007 are water-soluble, and all comprise cyclodextrin. All of the specific compositions disclosed in WO 2006/089007 comprise a covalent attachment between the bioactive moiety and the polymer.

WO 2006/089007 generally discloses the systemic administration of the compositions disclosed therein. The water soluble nature of the compositions disclosed in WO 2006/089007 means that they would not be suitable for topical application to a site in the body in contact with bodily fluids, as the composition would dissolve away from that site resulting in systemic administration of the composition. To provide targeted release of the biological moiety, WO 2006/089007 teaches that the compositions may include targeting ligands to assist the composition in targeting a particular target area, entering a particular target cell and/or binding to a target receptor. Biotin, monoclonal antibodies, steroidal lipids, nutrients and sugars are all taught as being suitable targeting ligands. However, regardless of whether the release of the biological moieties is targeted, the administration of the composition of WO 2006/089007 cannot be topical or site specific due to its water soluble nature.

WO 94/09826 discloses a photoactivatable drug delivery system in which a drug is combined with a photosensitive macromolecule. The drug is released, in therapeutically active form, upon appropriate irradiation. There is no disclosure that the photosensitive macromolecule may be attached to a polymer matrix through non-covalent interactions. There is also no suggestion in WO 94/09826 that the protecting group may be polymerised to form part of a polymer matrix. WO 94/09826 makes no suggestion of the use of a 3,5 dimethoxy-benzoin compound as the photosensitive macromolecule. The drug delivery composition of WO 94/09826 is not suitable to be formed into a drug delivery apparatus.

WO 96/23543 discloses a drug delivery device having at least one surface coated with a drug delivery composition. In particular, the drug delivery device may be a catheter, an endoscope or a polymer stent. The drug delivery device comprises an active ingredient photoreleasably linked to the surface of the drug delivery device. There is no teaching that the photoactivatable linking agent may be attached to the polymer matrix of the drug delivery composition through non-covalent interactions. There is also no suggestion that the photoactivatable linking agent may be a 3,5 dimethoxy benzoin compound. The drug delivery composition of WO 96/23543 is not suitable to be formed into a drug delivery apparatus.

The present invention relates to a molecular method for drug delivery of various classes of active ingredients, including antibiotics, analgesics, anti-histamines, nutraceuticals, antipyretics, non-steroidal anti-inflammatories, antiepileptics, neurotransmitters, steroidal and non-steroidal hormones and, antihistamines. The delivery of such active ingredients is triggered by exposure of the drug delivery device or composition to electromagnetic radiation at a predetermined wavelength and intensity. The drug dose delivered may be precisely controlled by controlling the amount of electromagnetic radiation the device or composition is exposed to. The drug delivery device or composition of the present invention acts as a molecular-scale drug dosing device, with control of delivery at the molecular scale, and potentially at the level of a single molecule of active ingredient.

According to a first aspect of the present invention there is provided a non-water soluble composition comprising a conjugate and a polymer matrix, said conjugate comprising an active ingredient bonded to a protecting group wherein exposure of the composition to electromagnetic radiation at a suitable pre-determined wavelength and intensity induces release of the active ingredient from the composition wherein the protecting group is substantially permanently retained in the polymer matrix.

Generally, the active ingredient is bonded to the protecting group via an ester, carbamate, amide, phosphonate ester, thioester or ether group. Typically the active ingredient is bonded to the protecting group via an ester or carbamate group wherein upon said exposure to electromagnetic radiation the ester group reacts to form a carboxylic acid group on the active ingredient or the carbamate group reacts to form a secondary amine group on the active ingredient.

The non-water soluble nature of the composition of the present invention, means that the composition may be applied topically in the body without risk of the composition dissolving into surrounding tissue, resulting in systemic administration. The application of the composition is site specific due to its non-water soluble nature, regardless of whether the composition is in contact with bodily fluids. This means that implantable drug delivery devices may comprise the composition of the present invention without risk of the composition being released into the body through dissolution of the composition into bodily fluids. The site specific action of the composition of the present invention allows targeted delivery of the active ingredient. In contrast, water soluble compositions (such as those disclosed in WO 2006/089007) dissolve into the aqueous environment of the body, resulting in non-specific administration of the composition, regardless of whether the release of biological moieties from the composition is targeted to specific areas or tissue types due to the incorporation of targeting ligands.

As used in the present specification, the term "non-water soluble" is intended to mean that the amount of the composition which can dissolve into free solution with water, biological fluids or other aqueous media including buffered media is negligible, typically 10 parts per million or less. The composition may comprise a hydrogel, being a polymer network which is capable of absorbing a significant proportion of water, biological fluids or other aqueous media including buffered media, but without itself dissolving in that medium.

As used in the present specification, the term "water soluble" is intended to mean the ability of the composition to dissolve, and thus to enter a single phase solution when exposed to water, biological fluids or other aqueous media including buffered media, whereby the composition is solvated by the solvent. Typically where the amount of the composition which can dissolved into free solution with water is more than ten parts per million the composition is considered to be water soluble. Suitably a water soluable composition dissolves into free solution with water at 50 parts per million or more; advantageously 75 parts per million or more; preferably 100 parts per million or more.

Preferably the polymer matrix does not comprise cyclodextrin.

Advantageously the polymer matrix is based on one or more of the following polymers:
polyolefins, for example, poly(ethylene), poly(propylene); vinyl polymers and copolymers, for example, poly(vinyl chloride), poly(vinyl pyrrolidoone); acrylate polymers and copolymers, for example, poly(2-hydroxyethyl methacrylate), poly(methyl methacrylate), poly(methacrylic acid), poly(acrylic acid), poly(diethylaminoethylmethacrylate), poly(diethylaminoethylethacrylate); elastomers, for example, silicone, styrene-isoprene/butadiene-styrene, latex; polyurethanes; polyesters, for example, poly(lactic acid), poly(glycolic acid), poly (lactic acid-co-glycolic acid), poly(caprolactone), poly (orthoesters); polyphosphazines.

The release of the active ingredient from the composition is preferably controllable and predictable. The release of the active ingredient is generally quantitative.

A high level of control can be exerted on electromagnetic radiation delivered to the composition in terms of control of the wavelength, and intensity of the electromagnetic radiation, and control of the duration, and location of the exposure. This high level of control can be exploited through a light-controlled drug liberation reaction to give control of the quantity of drug released (the dose), the timing of the release event, and its location. Importantly, this control potentially operates at the level of the single molecule, allowing dosing control of the delivery of the active ingredient at the molecular scale.

Suitably the active ingredient is released at an optimal therapeutic concentration over a prolonged period. Typically the rate of release of the active ingredient from the composition is constant throughout the exposure to electromagnetic radiation.

The protecting group may be any suitable compound that can bond to the active ingredient, suitably through the formation of an ester or carbamate bond. Preferably the protecting group is non-water soluble and generally it is retained by the polymer matrix upon release of the active ingredient.

In one embodiment, the protecting groups are substantially unreactive towards commonly employed acids and bases such as hydrochloric acid, sulfuric acid, acetic acid, citric acid, lactic acid, sodium hydroxide, calcium hydroxide, potassium hydroxide, triethylamine and ammonia.

Typically the protecting group is a photolabile benzoinyl, a nitro benzyl, dinitrobenzyl or trinitrobenzyl, a benzyloxycarbonyl, a 1-(2-nitrophenyl)ethyl, a nitroveratryl, a 6-nitroveratryloxycarbonyl, a methylnitropiperonyl, a phenacyl, an alkoxybenzoin, a 3,5-dimethoxybenzyl, group or a pivaloylglycol-based, a NpSSMpact system or a chromium arene-based system.

Advantageously the protecting group is dimethoxybenzoin; nitro benzyl ester; benzoinyl ester; benzoinyl carbamate; nitro benzyl; dinitrobenzyl; trinitrobenzyl; a derivative of an alcohol, carboxylic acid, amine, amide, phosphate, nucleoside or glycoside; a benzyloxycarbonyl derivative; a 1-(2-nitrophenyl)ethyl derivative of a phosphate, an amide, a carboxylic ester or an ether; or a 6-nitroveratryloxycarbonyl derivative. Preferably, the protecting group comprises a 3,5-Dimethoxybenzoin group (3,5-DMB).

The protecting group may be a substituted 3,5-DMB group; typically substituted with one or more vinyl or acrylate group.

The use of a protecting group comprising a Dimethoxybenzoin group, in particular a 3,5-DMB group, generally renders the composition water insoluble. The use of such a protecting group means that substantially all of the protecting group is retained in the polymer matrix following release of the active ingredient. Generally, where the protecting group comprises a 3,5-DMB group at least 95% of the protecting group is retained; suitably at least 99%; more suitably around 99.9%.

According to one embodiment of the present invention the release of the active ingredient proceeds as shown in Scheme 1 wherein the protecting group is based on 3,5-Dimethoxybenzoin ester and R represents an active ingredient.

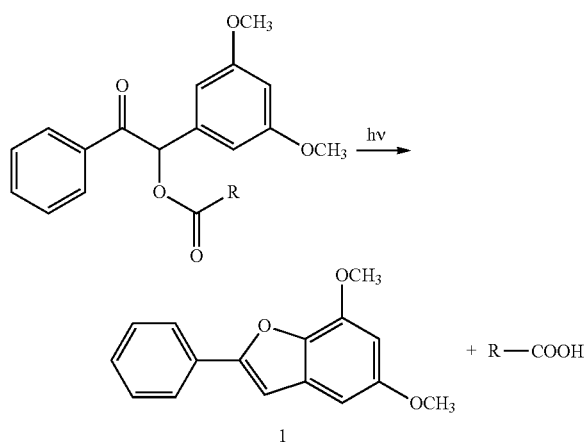

The active ingredient may be any compound exhibiting activity. Generally, the active ingredient comprises a carboxylic acid group or a secondary amine group. Suitably the active ingredient is water soluble.

In one embodiment the active ingredient is an antibiotic (in particular an anti-histamine antibiotic), an analgesic, a vitamin, an antimicrobial, an anti-histamine, an antipyretic a hormone (steroidal or non-steroidal), a neurotransmitter or a non-steroidal anti-inflammatory. Suitably the active ingredient is an analgesic, a non-steroidal anti-inflammatory, a neurotransmitter, a steroidal or non-steroidal hormone or an antihistamine. Preferably the active ingredient is acetyl salicyl, ibuprofen, ketoprofen, gentamicin, ciprofloxacin, diclofenac, nalidixic acid, ofloxacin, ciprofloxacin, erythromycin, clarithromycin, vancomycin, fexofenadine, desloratidine, levocetirizine, olopatadine, levocabastine, gamma-amino butyric acid, lidocaine, amethocaine, testosterone, cholesterol or oestrogen.

The conjugate may typically be in solid or liquid form before combination with the polymer matrix. When in solid form, the conjugate may be physically dispersed or dissolved in the polymer matrix.

The polymer matrix may typically be in the form of a hyrogel or gel.

Although in general, each protecting group is bonded to one active ingredient molecule, in some embodiments, more than one active ingredient molecule may be bonded to each protecting group.

The conjugate may be bonded to the polymer matrix, for instance through bonding of functional groups on the protecting groups to the polymer matrix. Alternatively the conjugate may form part of the polymer matrix, for instance through polymerization of the protecting groups. Generally the conjugate is retained in the polymer matrix through non-covalent interactions, such as, hydrogen bonds, Van der Waals attractions, π-π interactions, electrostatic interactions or combinations thereof.

The composition is generally in the form of a gel, in particular a hydrogel. Alternatively, the composition may be in the form of a polymer permeable to the active ingredient or permeable to a suitable solvent. In general, the glass transitional (Tg) behaviour and the corresponding mechanical properties of the surface-modified polymeric compositions of the present invention do not deviate largely from the corresponding unmodified polymers.

According to a further aspect of the present invention there is provided a non-water soluble drug delivery composition comprising a conjugate and a polymer matrix said conjugate comprising an active ingredient bonded to a protecting group via a first functional group, wherein exposure of the composition to electromagnetic radiation at a suitable pre-determined wavelength and intensity induces release of the active ingredient from the composition, wherein the protecting group comprises a second functional group attached to the polymer matrix generally through non-covalent interactions.

Where the protecting group is non-covalently attached to the polymer, the polymer does not require a specific functionality. This means that the composition may comprise a far greater range of polymers. In addition, the manufacture of the composition of the present invention is less complex where the protecting group is non-covalently linked to the polymer matrix. The manufacture of such compositions of the present invention requires less steps, and milder reaction conditions. In addition, compositions of the present invention, comprising a protecting group non-covalently attached to the polymer, are stable to conditions (such as hydrolytic environments) where covalent linking groups are likely to be cleaved, rendering the device comprising the composition inoperative.

The first functional group is generally an ester, carbamate, amide, phosphonate ester, thioester or ether group. Typically the first functional group is generally an ester or carbamate group wherein upon said exposure to electromagnetic radiation the ester group reacts to form a carboxylic acid group on the active ingredient or the carbamate group reacts to form a secondary amine group on the active ingredient.

Generally, the protecting group is substantially permanently incorporated into the drug delivery composition. As such, the protecting group is generally not released from the drug delivery composition throughout or following the exposure of the composition to electromagnetic radiation even if the composition is in contact with bodily fluids.

As detailed above, the non-water soluble nature of the compositions of the present invention allows site specific application of the compositions with minimal risk of the compositions dissolving away from the site of application. Furthermore, the non-water soluble nature of the compositions of the present invention allows the formation of drug delivery devices from the compositions described herein.

Preferably the polymer matrix does not comprise cyclodextrin.

Advantageously the polymer matrix is based on one or more of the following polymers:
  polyolefins, for example, poly(ethylene), poly(propylene); vinyl polymers and copolymers, for example, poly(vinyl chloride), poly(vinyl pyrrolidoone); acrylate polymers and copolymers, for example, poly(2-hydroxyethyl methacrylate), poly(methyl methacrylate), poly(methacrylic acid), poly(acrylic acid), poly(diethylaminoethylmethacrylate), poly(diethylaminoethylethacrylate); elastomers, for example, silicone, styrene-isoprene/butadiene-styrene, latex; polyurethanes; polyesters, for example, poly(lactic acid), poly(glycolic acid), poly(lactic acid-co-glycolic acid), poly(caprolactone), poly(orthoesters); polyphosphazines.

Typically the second functional group is one or more thiol, amino, alkylamino, mercapto, carboxylic acid or alcohol group, said second functional group being attached to the polymer matrix. More suitably, the second functional group is one or more alkylamino or mercapto functional group. Suitably the second functional group(s) is/are sterically unhindered.

Typically the polymer matrix comprises poly(vinyl chloride) (PVC); and the second functional group is attached thereto.

Typically, the second functional group(s) are amino or thiol groups and said second functional group(s) are attached to the polymer matrix (typically PVC) through nucleophilic substitution, generally through nucleophilic substitution of the terminal primary PVC.

Generally the protecting group comprises a 3,5-DMB group, typically substituted with one or more vinyl or acrylate groups.

The protecting group may comprise a spacer, such as an alkyl spacer, for attachment of the second functional group. The incorporation of the spacer will typically allow the protecting group to be electrically insulated from the polymer matrix. The predictable photophysical behaviour of the protecting group may be retained accordingly.

Preferably the composition as described above has the following structures where R represents the structure of the active ingredient:

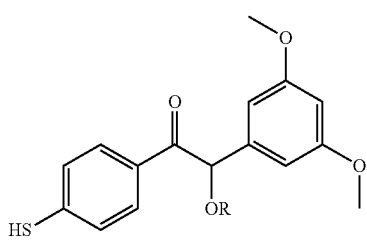

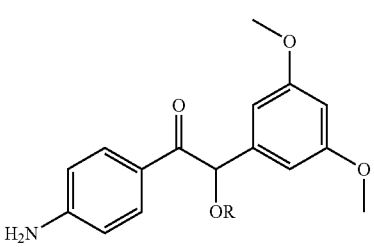

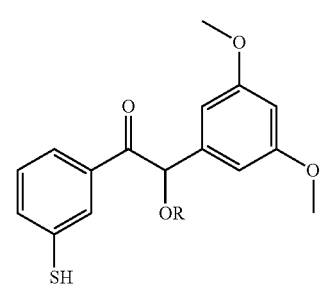

-continued

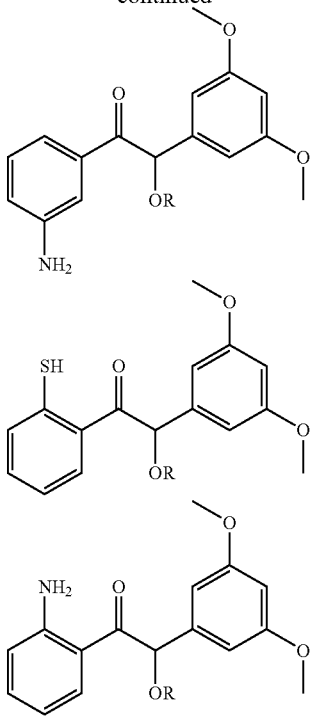

According to a further aspect of the present invention there is provided a non-water soluble drug delivery composition comprising an active ingredient, a protecting group and a polymer matrix said active ingredient being bonded the a protecting group wherein exposure of the composition to electromagnetic radiation at a suitable pre-determined wavelength and intensity induces release of the active ingredient from the composition, wherein the polymer matrix is formed from one or more copolymer compounds wherein the, or one of the, copolymer compounds comprises the protecting group.

Generally the active ingredient is bonded to the protecting group via an ester or carbamate group, wherein upon said exposure to electromagnetic radiation the ester group reacts to form a carboxylic acid group on the active ingredient or the carbamate group reacts to form a secondary amine group on the active ingredient.

Generally, the protecting group is substantially permanently incorporated into the drug delivery composition. As such, the protecting group is generally retained in the drug delivery composition throughout and following the exposure of the composition to electromagnetic radiation regardless of whether the drug delivery composition has been administered to or implanted in a human or animal body, and regardless of whether the drug delivery composition has been contacted with bodily fluids.

As detailed above, the non-water soluble nature of the compositions of the present invention allows site specific application of the compositions with minimal risk of the compositions dissolving away from the site of application. This allows targeted release of the active ingredient without the need for targeting ligands.

Preferably the polymer matrix does not comprise cyclodextrin.

Advantageously the polymer matrix is based on one or more of the following polymers:

polyolefins, for example, poly(ethylene), poly(propylene); vinyl polymers and copolymers, for example, poly(vinyl chloride), poly(vinyl pyrrolidoone); acrylate polymers and copolymers, for example, poly(2-hydroxyethyl methacrylate), poly(methyl methacrylate), poly(methacrylic acid), poly(acrylic acid), poly(diethylaminoethylmethacrylate), poly(diethylaminoethylethacrylate); elastomers, for example, silicone, styrene-isoprene/butadiene-styrene, latex; polyurethanes; polyesters, for example, poly(lactic acid), poly(glycolic acid), poly(lactic acid-co-glycolic acid), poly(caprolactone), poly(orthoesters); polyphosphazines.

Suitably the protecting group is a chemically protected alkylamino group (for example an N-BOC group for amino-functionalisation), or a thioalkyl Grignard reagent. Typically the protecting group is a photolabile benzoinyl, a nitro benzyl, dinitrobenzyl or trinitrobenzyl, a benzyloxycarbonyl, a 1-(2-nitrophenyl)ethyl, a nitroveratryl, a 6-nitroveratryloxycarbonyl, a methylnitropiperonyl, a phenacyl, an alkoxybenzoin, a 3,5-dimethoxybenzyl, group or a pivaloylglycol-based, a NpSSMpact system or a chromium arene-based system.

Advantageously the protecting group is a 3,5-dimethoxybenzoinyl group, a nitrobenzyl group, a dinitrobenzyl group, a trinitrobenzyl group, a benzyloxycarbonyl group or a nitroveratryloxycarbonyl group.

Suitably the, or one of the, copolymer compounds comprises the protecting group, vinyl monomers and/or acrylate monomers.

The copolymer may be a 3,5-DMB compound suitably comprising a pendant vinyl group; more suitably a pendant 2-vinyl group, a pendant 3-vinyl group or a pendant 4-vinyl group. Alternatively the copolymer may be a 3,5-DMB compound comprising a pendant acrylate group.

Suitably the monomer suitable for copolymerisation to form the polymer matrix has the following structure (where RCOOH or RR'NH represents the active substance):

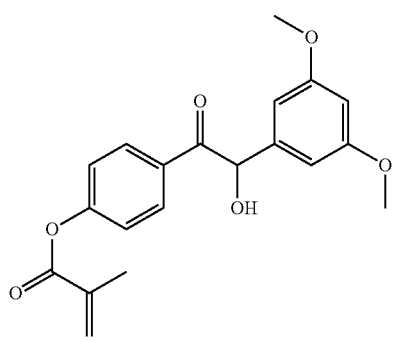

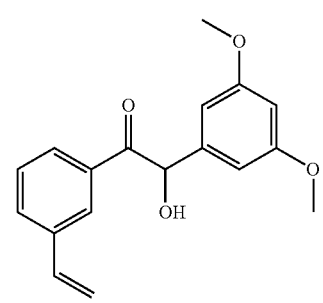

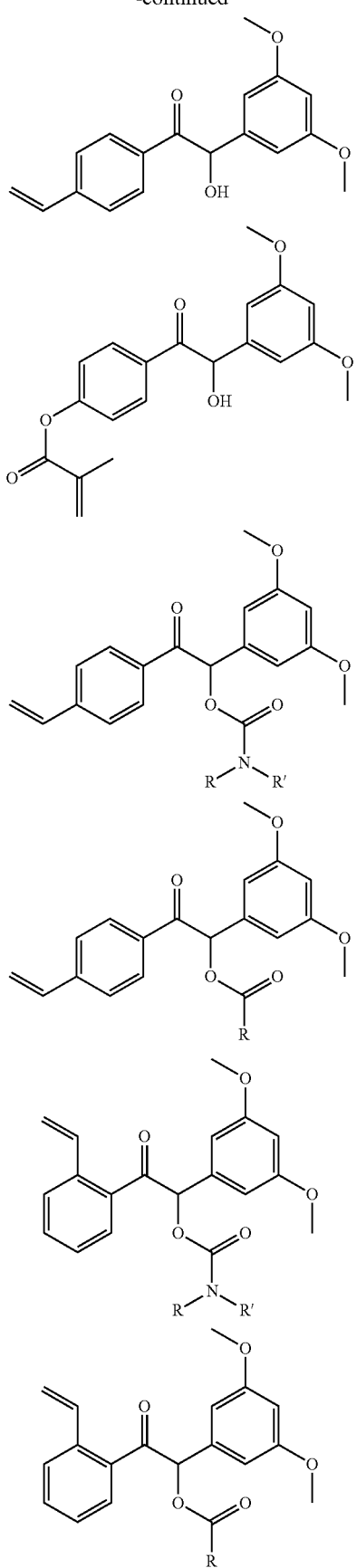

-continued

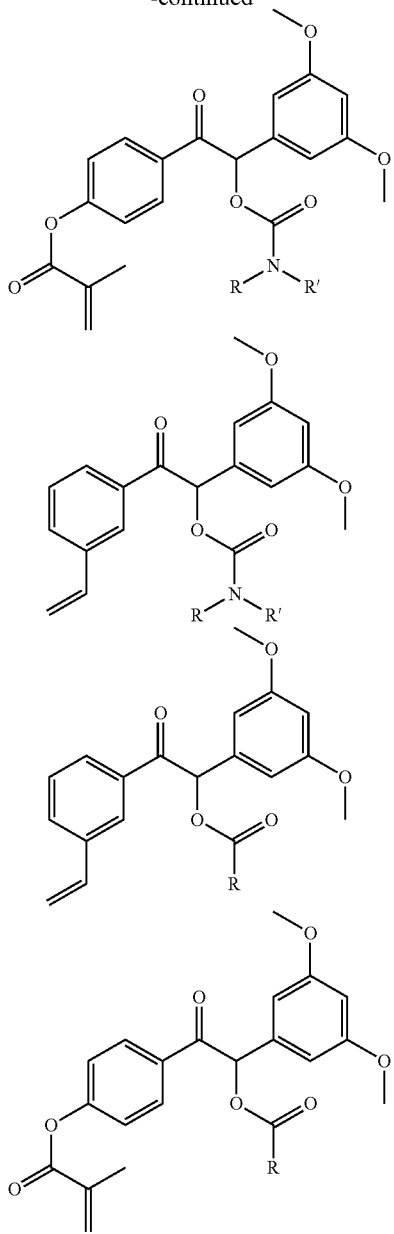

Suitably the copolymer, or one of the copolymers is comprised of poly(2-hydroxyethyl methacrylate), poly(methyl methacrylate), poly(methyl acrylate), poly(acrylamide), poly(methacrylic acid), poly(acrylic acid), poly(lactic acid), poly(glycolic acid), poly(vinyl alcohol) and copolymers derived from suitable mixtures of these monomers.

The wavelength of electromagnetic radiation the drug delivery composition is exposed to before release of the active ingredient is induced may be controlled by controlling the structure of the drug delivery composition. In particular, altering the structure of the protecting group alters the wavelength necessary to induce release of the active ingredient. Release is induced when the protecting group absorbs electromagnetic radiation and enters an electronically excited state. The wavelength appropriate for release for a given protecting group is thus dependent on the wavelength being capable of being absorbed electronically by the protecting group.

Where the protecting group comprises a 3,5-DMB group the wavelength necessary to induce release is typically 250 nm to 500 nm; suitably 250 nm to 470 nm; generally 300 nm to 400 nm. According to one embodiment, the wavelength necessary to induce release is 310 nm to 320 nm; preferably 312 nm. Alternatively, the wavelength necessary to induce release is 360 nm to 370 nm; preferably 365 nm. A composition in which release of the active ingredient is triggered upon contact with electromagnetic radiation having a wavelength of 360 nm to 370 nm is preferred as less tissue damage is likely.

The protecting group of any one of the compositions described above is substantially permanently incorporated into the polymer matrix and substantially none of the protecting group is released upon the exposure of the composition to electromagnetic radiation.

Typically 1% or less of the protecting group is released upon exposure of the composition to electromagnetic radiation for 10 hours; generally less than 0.5%; suitably less than 0.05%; more suitably less than 0.01%. Preferably less than 0.1 per hour of the protecting group is released from the composition upon the exposure to electromagnetic radiation.

The composition of the present invention may suitably be in the form of a tablet, capsule, suspension, cream, ointment, lotion, powder, gel, hydrogel, solution, paste, spray, foam, oil, enema, suppository, controlled or slow release matrix depot, subcutaneous implant, pessary, suppository, intravaginal device, intrauterine device and the like.

According to a further aspect of the present invention there is provided a method of medical treatment comprising the steps of administering any one of the drug delivery compositions as described above to a patient in need thereof and exposing the drug delivery composition to electromagnetic radiation at a predetermined wavelength and intensity suitable to induce release of the active ingredient from the drug delivery composition.

According to a further aspect of the present invention there is provided any one of the drug delivery compositions as described above for use in therapy.

According to a further aspect of the present invention, there is provided any one of the drug delivery compositions described above for use as a medicament.

According to a further aspect of the present invention there is provided any one of the drug delivery compositions described above for use in the treatment of the following diseases or conditions:
infection initially caused by bacteria, parasites, viruses or fungi such as urinary tract infection, pneumonia, ocular and skin infection, hypersensitivity, glaucoma, posterior capsular opacification, diabetes, epilepsy and pain.

According to a further aspect of the present invention there is provided the use of any one of the drug delivery compositions as described above in the manufacture of a medicament for the treatment of:
infection initially caused by bacteria, parasites, viruses or fungi such as urinary tract infection, pneumonia, ocular and skin infection, hypersensitivity, glaucoma, posterior capsular opacification, diabetes, epilepsy and pain.

According to a further aspect of the present invention there is provided a drug delivery device comprising one or more of the drug delivery compositions as described above.

The drug delivery device of the present invention may be in the form of a medical or non-medical drug delivery device or apparatus.

Typically the drug delivery device is in the form of any device or apparatus having a structural, for example, a "mechanical" function, which device or apparatus is suitable for temporary or permanent implantation in, or for attachment in or on, the human or animal body, the device or apparatus being exemplified by, but by no means limited to, urinary tract devices (including ureteral stents and urinary catheters), ocular devices (including contact lenses), intraocular lenses, orthopaedic devices, respiratory devices (including endotracheal tubes), cardiovascular devices, dental devices, neurological devices, gastrointestinal devices, audiology devices, surgical devices, including surgical gloves, foot care devices, wound healing devices, condoms and the like. In addition, the term "medical device" is intended, in the present invention, to comprise devices having drug delivery functions, in addition to the aforementioned structural (or mechanical) functions. Drug delivery is intended to mean any device arranged to permit drug delivery therefrom, the device being exemplified by, but by no means limited to, subcutaneous implants, pessaries, suppositories, intravaginal devices, intrauterine devices, intrarectal devices, transdermal devices, wound care devices and the like.

Suitably the medical device or apparatus is selected from apheresis equipment, blood bags; blood administration tubing; extracorporeal membrane oxygenation equipment; dialysis and peritoneal drainage bags; urinary collection bags; urological catheters; wound drainage bags and tubes; enteral feeding equipment; nasogastric tubes; breast pump tubes; intravenous catheters, drip chambers, tubing and solution bags; total parenteral nutrition bags; hemodialysis tubing and catheters; film wrap; gloves; endotracheal tubes; tracheostomy tubes; esophagel tubes; humidifiers; ocular prosthesis; or sterile water bags and tubing.

Advantageously the drug delivery device or apparatus is in the form of a catheter, implant (suitably subcutaneous implant), contact lens, endotracheal (ET) tube, intraocular lens (IOL), cutaneous or sub-cutaneous device for delivery or oral gel.

Typically the drug delivery device or apparatus is in the form of a catheter, contact lens, ET tube or intraocular lens.

Alternatively, the drug delivery device or apparatus may be in the form of a non-medical drug delivery device such as a polymeric implant.

Generally the induction and rate of release of the active ingredient from the drug delivery device or apparatus of the present invention is precisely controllable and predictable.

The drug delivery device or apparatus of the present invention may have contact with the bodily fluids of the patient treated. In particular the drug delivery device or apparatus may have contact with blood, urine or fluids of the eye of the patient treated.

As the drug delivery compositions of the present invention are non-water soluble, they do not dissolve to any significant extent into bodily fluids upon contact therewith.

Suitably, only the active ingredient is released from the drug delivery device, and the rest of the drug delivery composition is retained in or on the drug delivery device or apparatus for 28 days, typically following implantation of the drug delivery device or apparatus for three months. Generally at least 95% of the drug delivery composition suitably more than 98% of the drug delivery composition; advantageously around 99.5% of the composition is retained on, or in the drug delivery device or apparatus following implantation of the drug delivery device or apparatus for up to 28 days; suitably up to 3 months.

As noted above, bacteria can colonise medical device polymers and develop extreme antibiotic resistance rapidly by exuding an enveloping, protective exopolysaccharide matrix and entering into a very reduced metabolic mode of existence. Suitably the drug delivery device or apparatus of the present invention reduces adherence of bacteria during or following delivery of the active ingredient. In particular, the drug delivery device or apparatus suitably reduces colonization and adherence of bacterial isolates and reduces the development of a biofilm during or following delivery of the active ingredient.

Suitably the drug delivery device or apparatus is formed from a material comprising one or more of the drug delivery compositions as described above.

According to one embodiment of the present invention the drug delivery device or apparatus is formed from a material consisting essentially of one or more of the drug delivery compositions as described above.

Known drug delivery devices allowing sustained release of active ingredients generally comprise a coating of a drug delivery composition. In contrast, drug delivery devices or apparatus of the present invention may be formed from the drug delivery composition. As such, the drug delivery composition may form an integral part of the drug delivery devices or apparatus of the present invention. Forming the drug delivery device or apparatus from the drug delivery composition minimises the complexity, expense and time associated with the manufacture of the drug delivery devices or apparatus as the step of applying a drug delivery composition after formation of the drug delivery device or apparatus is avoided. It is difficult to ensure a constant distribution of drug delivery composition over the whole surface of known drug delivery devices. In particular, it is very difficult to apply an even coating on known drug delivery devices having an intricate or complex shape, for instance including sharp corners or narrow passages. Drug delivery devices having an intricate or complex shape include, for instance, catheters, orthopaedic devices, respiratory devices (including ET tubes) and surgical devices. As such, known drug delivery devices can be associated with inconsistent and unpredictable release of the active ingredient from different areas of the surface of each drug delivery device as well as inconsistent and unpredictable release of the active ingredient throughout any batch manufactured. These problems are associated with regulatory concerns, as well as with increased time and complexity of manufacture. The problems of ensuring a constant distribution of drug delivery composition are avoided if the drug delivery device is formed from the drug delivery composition itself. The rate of release of active ingredient from the drug delivery devices or apparatus of the present invention is controllable and predictable, and is easily engineered to be constant throughout the drug delivery device or apparatus. Alternatively, the rate of release of the active ingredient from the drug delivery device or apparatus of the present invention may be engineered to differ depending on the area of the drug delivery composition. For instance, according to one embodiment of the present invention, the rate of release of the active ingredient from the interior lumen of a urinary catheter is high relative to the rate of release from the other surfaces of the urinary catheter.

As the drug delivery device or apparatus of the present invention may be formed from the drug delivery composition, the duration of release of the active ingredient may be longer than known drug delivery devices. The drug delivery composition may form an integral part of the drug delivery device or apparatus of the present invention. As such, the drug delivery composition may migrate from the drug delivery device or apparatus less than for known drug delivery devices and the retention of the drug delivery composition on the drug delivery device or apparatus of the present invention may be greater than for known drug delivery devices.

It is noted that a drug delivery device could not be formed from a water soluble drug delivery composition as described in WO 2006/089007.

According to one embodiment of the present invention, the non-water soluble drug delivery composition comprises a polymer matrix including a copolymer comprising 2-(hydroxyethyl)methacrylate and methyl methacrylate. The copolymer may be crosslinked, typically with a cross-linking agent such as ethylene glycol dimethacrylate, suitably at concentrations of up to 10% w/w.

According to one aspect of the present invention there is provided a drug delivery device or apparatus formed from a polymer, wherein the polymer comprises any one of the drug delivery compositions described above.

Suitably the polymer has the following structure:

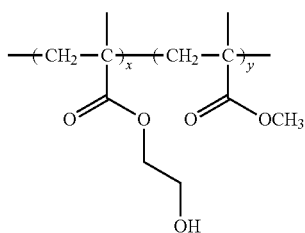 [SMILES: CCC(C)(CC(C)(C)C(=O)OC)C(=O)OCCO]

According to a further aspect of the present invention, the drug delivery device or apparatus may be coated with any one of the drug delivery compositions as described above.

Suitably the entire surface of the drug delivery device or apparatus is coated with any one of the drug delivery compositions described above.

Alternatively a portion of the surface of the drug delivery device or apparatus may be coated with any one of the drug delivery compositions described above.

Typically the drug delivery device or apparatus may be in the form of a catheter and the interior lumen may be coated with any one of the drug delivery compositions described above.

Typically the drug delivery device or apparatus may be in the form of a contact lens and 90 to 100% of the surface is preferably coated with the drug delivery composition.

According to a further aspect of the present invention there is provided a method of forming a drug delivery device or apparatus comprising the steps of:
  forming a mixture comprising at least one of the drug delivery compositions described above;
  forming a drug device or apparatus suitable for drug delivery from the mixture.

The production of some compositions requires specific methods of production where stirring rates are controlled to give a homogeneous distribution in the final composition. Most methods are straightforward however.

According to a further aspect of the present invention there is provided a method of forming a drug delivery device or apparatus comprising the steps of:
  forming a device or apparatus suitable for drug delivery;
  coating at least a portion of the surface of the device or apparatus with any one of the drug delivery compositions described above.

According to a further aspect of the present invention there is provided a method of releasing an active ingredient from a drug delivery device or apparatus at a controllable and predictable rate comprising the steps of:
  forming any one of the drug delivery compositions as described above;
  incorporating the drug delivery composition in a device or apparatus suitable for drug delivery to form a drug delivery device or apparatus; applying the drug delivery device or apparatus to a human or animal body (typically through implantation); and
  exposing the drug delivery device or apparatus to electromagnetic radiation at a suitable predetermined wavelength and intensity.

The drug delivery device or apparatus may be implanted into the body of a patient to be treated. The drug delivery device or apparatus is suitably exposed to electromagnetic radiation following implantation.

In general, drug delivery is triggered in known drug delivery devices and compositions indirectly, and a macroscopic change is induced in the matrix into which the drug is incorporated. In contrast, drug delivery is directly triggered in the drug delivery devices and compositions of the present invention. The structure and integrity of the polymer matrix is generally maintained throughout exposure of the drug delivery device or drug delivery composition to electromagnetic radiation. Typically the only change this exposure induces is to alter the bond between the active ingredient and the protecting group from an ester group to a carboxylic group on the active ingredient, or alternatively from a carbamate group to a secondary amine group on the active ingredient.

The structure of the polymer matrix generally remains intact throughout exposure to electromagnetic radiation and only the ester or carbamate linkage bonding the active ingredient to the protecting group is affected through exposure to the electromagnetic radiation.

The initiation of the release of the active ingredient and the rate of the release of the active ingredient are generally precisely controllable and predictable in accordance with pharmacological demands.

Typically the active ingredient is released at a rate of 0.08 to 0.10/s, suitably 0.08 to 0.09/s, advantageously 0.083/s. The active ingredient is generally released quantitatively.

The rate of release of the active ingredient may be precisely controlled by controlling the amount of electromagnetic radiation the drug delivery device or drug delivery composition is exposed to.

Generally, upon sufficient exposure to electromagnetic radiation at least 95% of the active ingredient is released from the drug delivery composition, typically more than 99%. Preferably upon sufficient exposure to radiation substantially all of the active ingredient is released from the drug delivery composition.

The method as described above wherein the rate of release of the active ingredient is substantially constant.

The delivery of the active ingredient typically stops upon removal of the electromagnetic radiation from the drug delivery composition or device.

Electromagnetic radiation is a particularly desirable external trigger for the release of the active ingredient as the electromagnetic radiation may be controlled very precisely. The wavelength, amplitude and intensity of the electromagnetic radiation to which the drug delivery devices, or apparatus and compositions of the present invention are exposed may be controlled very precisely. Furthermore, the precise location and intensity of the exposure may be controlled suitably through the use of the instruments such as appropriate light sources or fibre optics.

In one embodiment, the rate of release of the active ingredient is controllable through the control of one or more of the intensity, amplitude and wavelength of the electromagnetic radiation or the control of one or more of the duration and location of the exposure.

The release of the active ingredient may be activated upon exposure of the composition to UV electromagnetic radiation. Typically release is activated upon exposure to electromagnetic radiation having a wavelength of 200 to 300 nm, suitably a wavelength of 365 nm. Alternatively the wavelength may be 254 nm, 312 nm or combinations thereof.

Generally, release of the active ingredient is activated upon exposure to electromagnetic radiation having an amplitude of 0.05-300 W.

The release of the active ingredient may be induced under relatively mild conditions, for instance exposure of the drug delivery device or composition to low power (such as 15 W) 365 nm radiation at a distance of 1 cm.

Typically release of the active ingredient is activated upon exposure to electromagnetic radiation having an intensity of 15 W.

Suitably the exposure lasts for 0.1 s-30 mins. Typically the effect of the electromagnetic radiation is very localized. Preferably the effect of the exposure is localized to 0-5 cm from the site of the exposure.

The release of the active ingredient generally stops upon removal of the electromagnetic radiation.

Preferably the protecting group is retained in the composition or in the drug delivery device or apparatus throughout and following exposure to electromagnetic radiation.

Typically the protecting group is retained in the polymer matrix through attractions such as hydrogen bonds, covalent bonds or ionic bonds, or lack of solubility of the protecting group in the medium into which the active ingredient is released. Generally the protecting group is retained in the polymer matrix through non-covalent interactions such as hydrogen bonds and Van der Waals interactions. The protecting group is typically substantially insoluble in aqueous media.

The protecting group is suitably retained in the polymer matrix throughout and following the exposure of the composition to electromagnetic radiation. Typically less than 5% of the protecting group is released from the composition, generally less than 1%, advantageously less than 0.05%.

Where the protecting group is substantially permanently incorporated into the polymer matrix the amount of protecting group released throughout the exposure may be substantially less, typically less than 0.01%.

A method of treating a patient comprising the steps of administering the drug delivery device or apparatus as described above to the patient and exposing the drug delivery device or apparatus to electromagnetic radiation at a predetermined wavelength and intensity suitable to induce release of the active ingredient from the drug delivery device or apparatus.

Generally the drug delivery device or apparatus is administered through implantation.

According to a further aspect of the present invention, there is provided the drug delivery device or apparatus as described above for use in therapy, or for use as a medicament.

According to a further aspect of the present invention, there is provided the drug delivery device or apparatus as described above for use in the treatment of the following diseases or conditions:
infection initially caused by bacteria, parasites, viruses or fungi such as urinary tract infection, pneumonia, ocular and skin infection, hypersensitivity, glaucoma, posterior capsular opacification, diabetes, epilepsy and pain.

According to a further aspect of the present invention, there is provided the use of the drug delivery device or apparatus as described above in the manufacture of a medicament for the treatment of the following diseases or conditions:
infection initially caused by bacteria, parasites, viruses or fungi such as urinary tract infection, pneumonia, ocular and skin infection, hypersensitivity, glaucoma, posterior capsular opacification, diabetes, epilepsy and pain.

According to a further aspect of the present invention, there is provided a method of administering an active ingredient to a patient in need thereof comprising the steps of administering any one of the drug delivery compositions described above, or administering the drug delivery device or apparatus described above to the patient, and, exposing the drug delivery composition or device to electromagnetic radiation at a predetermined wavelength and intensity suitable to induce release of the active ingredient from the drug delivery composition, device or apparatus.

Typically the drug delivery compositions described above are administered to a patient through the implantation of a drug delivery device or apparatus comprising any one of the drug delivery compositions.

A method of forming a drug delivery composition as described above comprising the steps of:
reacting a protecting group with an active ingredient to form a conjugate;
incorporating the conjugate into a polymer matrix.

Advantageously the active ingredient is bonded to the protecting group via an ester or carbamate group.

The ester group linkage between the active ingredient and the protecting group may be formed directly or the formation of the ester group linkage may be mediated by standard esterification reagents such as DCC.

The carbamate group linkage between the active ingredient and the protecting group may be formed via N,N'-carbonyl diimidazole (CDI) mediated coupling wherein the CDI mediated coupling may optionally take place in the presence of methyltriflate. Alternatively, the carbamate group linkage may be formed using dimethylaminopyridine followed by contact with p-nitrophenylchloroformate together with the active ingredient (said active ingredient comprising a secondary amine).

The method may take place in the presence of catalysts such as methyl triflate.

A method of forming a composition as described above comprising the steps as shown in Scheme 2:

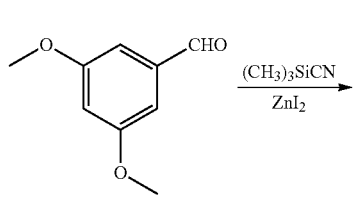

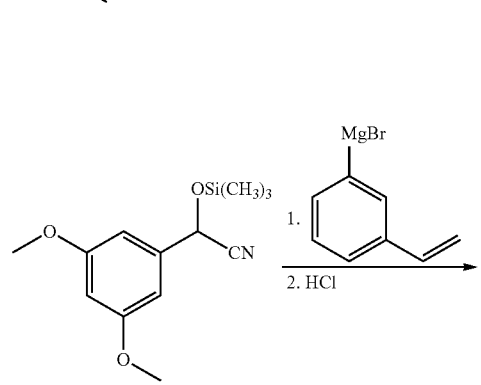

-continued

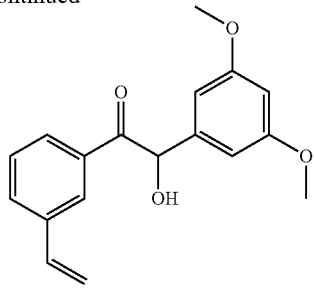

According to a further aspect of the present invention there is provided a method of forming a precisely controllable drug delivery device or apparatus comprising incorporating any one of the drug delivery compositions as described above in a device or apparatus suitable for drug delivery.

According to a further aspect of the present invention there is provided a method of substantially permanently incorporating a protecting group into a polymer matrix, said protecting group being bonded to an active ingredient via a first functional group wherein the protecting group comprises a second functional group, said method comprising the steps of reacting the protecting group with the polymer matrix to form bonds between the second functional group and the polymer matrix to form a drug delivery composition, wherein said active ingredient is releasable from the drug delivery composition upon exposure of the drug delivery composition to electromagnetic radiation at a suitable predetermined wavelength and intensity.

Typically the first functional group is an ester, carbamate, amide, phosphonate ester, thioester or ester group. Suitably the first functional group is an ester or carbamate linkage.

According to a further aspect of the present invention there is provided a method of substantially permanently incorporating a protecting group into a polymer matrix wherein the protecting group is bonded to an active ingredient, said method comprising the steps of:
  forming a copolymer comprising the protecting group,
  polymerising the copolymer to form the polymer matrix,
  wherein said active ingredient is releasable from the polymer matrix in a controllable and predictable manner upon exposure of the polymer matrix to electromagnetic radiation at a suitable predetermined wavelength and intensity.

Typically the protecting group is bonded to the active ingredient via an ester or carbamate linkage.

The method as described above wherein the protecting group is a chemically protected alkylamino compound (for example an N—BOC group for amino functionalisation), or a thioalkyl Grignard reagent.

Preferably the copolymer is mixed with vinyl or acrylate monomers or combinations thereof prior to polymerisation.

Preferred features and embodiments of each aspect of the invention are as for each of the other aspects mutatis mutandis unless context demands otherwise.

Figure 2:
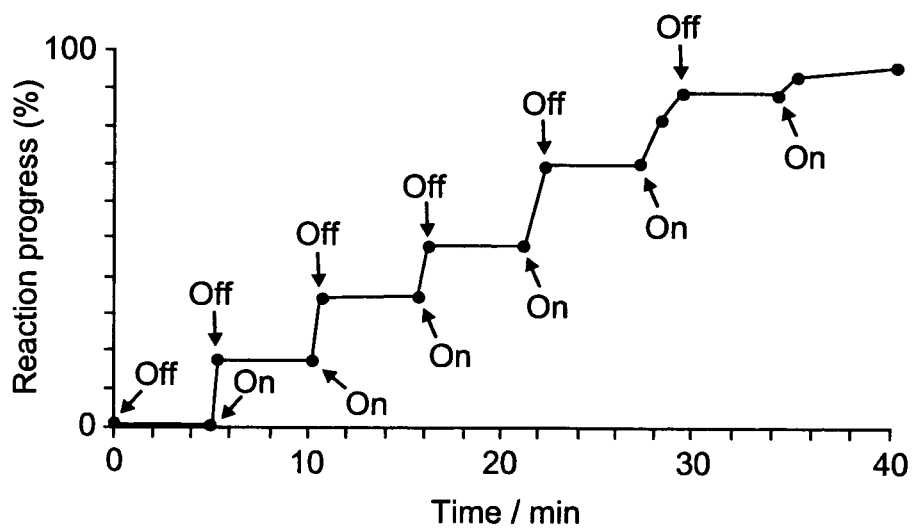

The present invention will now be described by way of Example only with reference to the accompanying figures wherein:

FIG. 1 shows a UV-visible absorption spectra of a conjugate comprising an ester of ibuprofen and 3,5-Dimethoxybenzoin (compound 2) after periods of irradiation of 0, 15, 30, 60, 120, 180, 240, 300, 360, 480, 600, 1200 and 1800s using 365 nm light; trends in absorbance with time are indicated by arrows;

FIG. 2 shows how the release of the active ingredient from a conjugate comprising an ester of ibuprofen or acetyl salicyl and 3,5-Dimethoxybenzoin (compound 1 and 2 respectively) differs upon exposure to light, and removal of the light source where "on" indicates a period of light exposure and "off" indicates the removal of the light source.

We use either dicylcohexylcarbodiimide-mediated or direct, acid chloride esterification methods to synthesize light-sensitive conjugates 2-4 of three model drugs; acetyl salicylic acid, ibuprofen, and ketoprofen, respectively (Chart 1).

The behaviour of 2-4 is characterised by irradiating a solution using 365 nm UV-A radiation. UV-visible spectra of a solution of 3 are shown in FIG. 1. As the photochemical reaction proceeds, the UV-visible spectrum of the reaction mixture changes (FIG. 1), reflecting the formation of 1 and drug and the consumption of conjugate. The solution absorption spectrum exhibits a band at 300 nm assigned to 5,7-dimethoxy-2-phenylbenzofuran 1.11. The isosbestic points at 231 and 262 nm indicate the reaction proceeds with no side products. The identity of reaction products was verified by chromatographic separation, followed by spectroscopic analysis to be solely the corresponding drug and 1. The reaction proceeded in an analogous fashion to related nondrug examples 12 and all three conjugates 2-4 behaved similarly.

A solution of 2 in acetonitrile was then exposed to alternating periods of light and dark using the same conditions for light conditions as previously. Precise control of the drug liberation, and hence dosing, is demonstrated by monitoring the progress of the reaction of 2 after various periods of exposure to light and dark conditions, shown in FIG. 2. The distinctive "stepped" profile of the reaction progress shows that the drug liberation reaction proceeds under light conditions, and that in dark conditions liberation of drug is stopped completely. The dose of liberated drug thus correlates with the duration of exposure to light. In this example, six periods of dosing and nondosing are alternated; this can be extended to any discrete dose required, in principle to the level of control provided from the light source, which includes molecule-scale control from low bursts of light deliverable from a laser source.

All documents referred to in this specification are hereby incorporated by reference. Various modifications and variations to the described embodiments of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A non-water soluble drug delivery composition comprising:
  a conjugate and a polymer matrix said conjugate comprising an active ingredient R bonded to a protecting group via a first functional group;
  wherein exposure of the composition to electromagnetic radiation at a suitable predetermined wavelength and intensity induces release of the active ingredient from the composition; and
  wherein the protecting group is selected from the group consisting of:

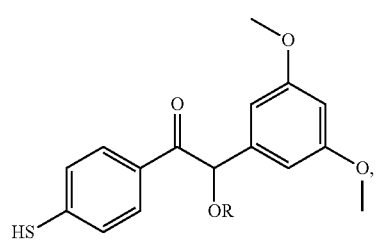

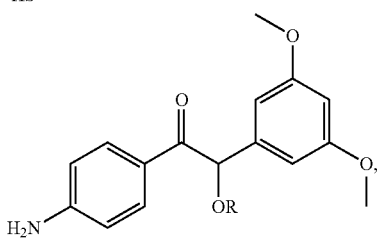

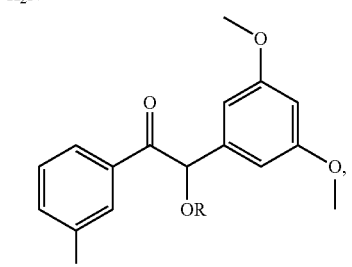

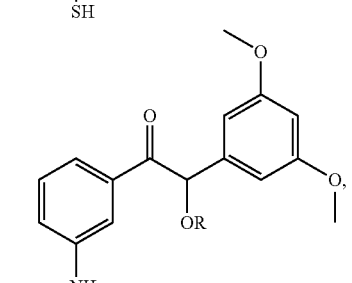

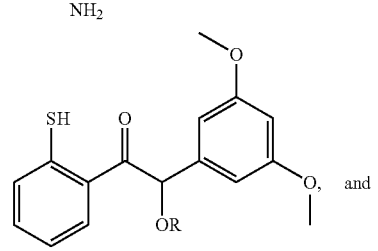

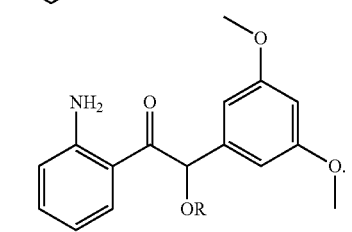

2. A non-water soluble drug delivery composition comprising:
   an active ingredient R;
   a protecting group; and
   a polymer matrix,
   wherein the active ingredient is conjugated to the protecting group;

wherein exposure of the composition to electromagnetic radiation at a suitable predetermined wavelength and intensity induces release of the active ingredient from the composition;

wherein the polymer matrix is formed from one or more copolymer compounds;

wherein the one or more of the copolymer compounds comprises the protecting group;

wherein the protecting group is covalently bonded to the one or more copolymer compounds; and wherein the protecting group is selected from the group consisting of

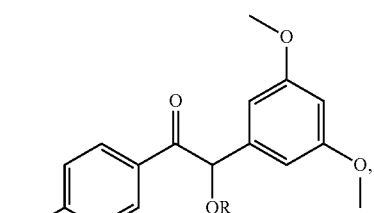

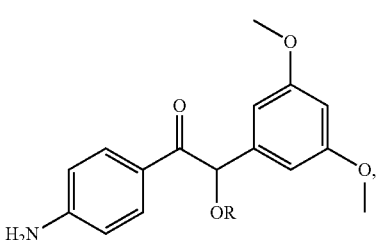

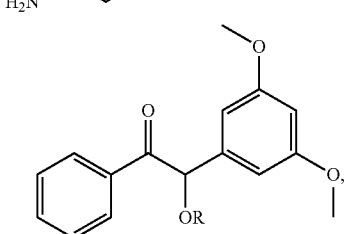

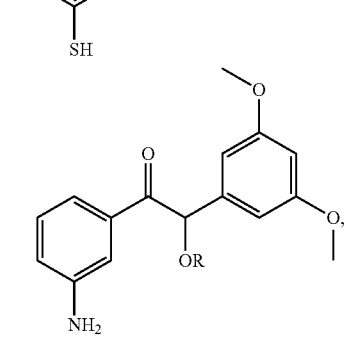

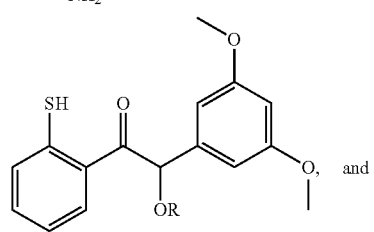

and

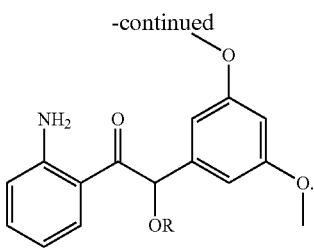

3. The composition as claimed in claim 1, wherein the active ingredient is bonded to the protecting group via an ester and wherein upon said exposure to electromagnetic radiation the ester group reacts to form a carboxylic acid group on the active ingredient.

4. The composition as claimed in claim 1, wherein the polymer matrix does not comprise cyclodextrin.

5. The composition as claimed in claim 1, dissolving 5 parts per million or less in water.

6. The composition as claimed in claim 1, wherein non-covalent interactions comprise at least one of hydrogen bonds, Van der Waals attractions, π-π interactions, electrostatic interactions or combinations thereof.

7. The composition as claimed in claim 1, wherein the polymer matrix comprises one or more of, poly(ethylene), poly(propylene), polyvinyl chloride), polyvinyl pyrrolidoone), poly(2-hydroxyethyl methacrylate), poly(methyl methacrylate), poly(methacrylic acid), poly(acrylic acid), poly(diethylaminoethylmethacrylate), poly(diethylaminoethylethacrylate), silicone, styrene-isoprene/butadiene-styrene, poly(lactic acid), poly(glycolic acid), poly(lactic acid-co-glycolic acid), poly(caprolactone), poly(orthoesters) and; polyphosphazines.

8. The composition as claimed in claim 1 in the form of a tablet, capsule, suspension, cream, ointment, lotion, powder, gel, solution, paste, spray, foam, oil, enema, suppository, controlled or slow release matrix or depot.

9. The composition as claimed in claim 1, wherein the active ingredient is an antibiotic, analgesic, vitamin, antihistamine, antimicrobial, an anti-histamine, an antipyretic, a hormone, a neurotransmitter or a non-steroidal anti-inflammatory.

10. The composition as claimed in claim 9, wherein the active ingredient is acetyl salicyl, ibuprofen, ketoprofen, gentamicin, ciprofloxacin, diclofenac, nalidixic acid, ofloxacin, ciprofloxacin, erythromycin, clarithromycin, vancomycin, fexofenadine, desloratidine, levocetirizine, olopatadine, levocabastine, gamma-amino butyric acid, lidocaine, amethocaine, testosterone, cholesterol or oestrogen.

11. The composition as claimed in claim 1, wherein the protecting group is substantially permanently incorporated into the polymer matrix and substantially all of the protecting group is retained in the composition throughout and following the exposure of the composition to electromagnetic radiation.

12. The composition as claimed in claim 2, wherein one or more of the copolymer compounds comprises vinyl or acrylate monomers or combinations thereof.

13. A drug delivery apparatus comprising the composition as claimed in claim 1.

14. The drug delivery apparatus of claim 13 in the form of: apheresis equipment, blood bags; blood administration tubing; extracorporeal membrane oxygenation equipment; dialysis and peritoneal drainage bags; urinary collection bags; urological catheters; wound drainage bags and tubes; enteral feeding equipment; nasogastric tubes; breast pump tubes; intravenous catheters, drip chambers, tubing and solution bags; total parenteral nutrition bags; hemodialysis tubing and catheters; film wrap; gloves; endotracheal tubes; tracheostomy tubes; esophageal tubes; humidifiers; ocular prosthesis; or sterile water bags and tubing.

15. The drug delivery apparatus as claimed in claim 13, wherein the apparatus is formed from a material comprising the composition as claimed in claim 1.

16. The drug delivery apparatus of claim 13, wherein the apparatus is formed from a material consisting essentially of the composition as claimed in claim 1.

17. The drug delivery apparatus as claimed in claim 13, comprising a coating of the composition as claimed in claim 1.

18. A method of administering an active ingredient to a patient in need thereof comprising the steps of administering the drug delivery apparatus as claimed in claim 13 to the patient, and exposing the drug delivery apparatus to electromagnetic radiation at a predetermined wavelength and intensity suitable to induce release of the active ingredient from the drug delivery apparatus.

19. The method as claimed in claim 18, wherein the structure and integrity of the polymer matrix is maintained throughout exposure of the drug delivery apparatus to electromagnetic radiation.

20. The method as claimed in claim 18, wherein the rate of release of the active ingredient is predicatable and controllable.

21. The method as claimed in claim 18, wherein the rate of release of the active ingredient is controlled through controlling the wavelength, amplitude and intensity of the electromagnetic radiation or the location and duration of the exposure to electromagnetic radiation.

22. The method as claimed in claim 18, wherein the rate of release of the active ingredient is substantially constant.

23. The method as claimed in claim 18, wherein the release of the active ingredient is stopped and started repeatedly through stopping and starting exposure of the drug delivery apparatus to electromagnetic radiation.

24. The method as claimed in claim 18, wherein at least 99% of the protecting group is retained in the drug delivery apparatus throughout the exposure of the drug delivery apparatus to electromagnetic radiation.

25. The method as claimed in claim 24, wherein at least 99.95% of the protecting group is retained in the drug delivery apparatus throughout the exposure of the drug delivery apparatus to electromagnetic radiation.

26. A method of treating a patient in need thereof comprising the steps of administering the drug delivery apparatus as claimed in claim 13 to the patient and exposing the drug delivery apparatus to electromagnetic radiation at a predetermined wavelength and intensity suitable to induce release of the active ingredient from the drug delivery apparatus.

27. The method as claimed in claim 26, wherein the method is for the treatment of the following diseases or conditions: urinary tract infection, pneumonia, ocular and skin infection, hypersensitivity, glaucoma, posterior capsular opacification, diabetes, epilepsy and pain.

28. The drug delivery apparatus as claimed in claim 13 for use in the treatment of the following diseases or conditions: urinary tract infection, pneumonia, ocular and skin infection, hypersensitivity, glaucoma, posterior capsular opacification, diabetes, epilepsy and pain.

29. The method of forming a drug delivery device as claimed in claim 13, comprising incorporating the composition as claimed in claim 1 in an apparatus suitable for drug delivery.

30. The method as claimed in claim 29, wherein the apparatus suitable for drug delivery is formed from a material and the composition is incorporated into the material prior to formation of the drug delivery apparatus.

31. The method as claimed in claim 29, wherein the composition is coated onto at least a portion of a surface of the apparatus suitable for drug delivery.

* * * * *